United States Patent [19]

Sovak et al.

[11] 4,341,756
[45] Jul. 27, 1982

[54] NOVEL AMINO-DIOXEPANE INTERMEDIATES FOR THE SYNTHESIS OF NEW NON-IONIC CONTRAST MEDIA

[75] Inventors: Milos Sovak, La Jolla; Ramachandran Ranganathan, San Diego, both of Calif.

[73] Assignee: The Regents of the University of California, Berkeley, Calif.

[21] Appl. No.: 141,097

[22] Filed: Apr. 17, 1980

Related U.S. Application Data

[63] Continuation-in-part of Ser. No. 117,151, Jan. 31, 1980, abandoned.

[51] Int. Cl.$^3$ .................... A61K 29/02; C07C 103/78
[52] U.S. Cl. ...................................... 424/5; 549/347; 564/153
[58] Field of Search ........................... 424/5; 564/153; 260/338

[56] References Cited

U.S. PATENT DOCUMENTS 4,021,481  5/1977  Almen et al. ...................... 564/153
4,239,747  12/1980  Pfeiffer et al. ...................... 564/153

FOREIGN PATENT DOCUMENTS 2628517  1/1978  Fed. Rep. of Germany ...... 564/153

Primary Examiner—Robert Gerstl
Attorney, Agent, or Firm—Bertram I. Rowland

[57] ABSTRACT

Novel intermediates for non-ionic polyiodo amino-substituted benzenepolyamides having polyol substituents on the amide nitrogens are provided which are 5-amino-6-hydroxy-1,3-dioxepanes. The compounds provide an economic and efficient route to novel contrast media having excellent chemical and physiological properties.

Also provided are methods for preparing the subject compounds.

31 Claims, No Drawings

NOVEL AMINO-DIOXEPANE INTERMEDIATES FOR THE SYNTHESIS OF NEW NON-IONIC CONTRAST MEDIA

The invention described herein was made in the course of work under a grant from the Department of Health, Education, and Welfare.

CROSS-REFERENCE TO RELATED APPLICATIONS

This application is a continuation-in-part of application Ser. No. 117,151 filed Jan. 31, 1980, now abandoned, which is hereby incorporated by reference.

BACKGROUND OF THE INVENTION

1. Field of the Invention

There are many applications for small highly functionalized water soluble organic compounds. Such compounds find use as a stem for the preparation of nonionic detergents, as buffers, or water solubilizing substituents. In the last situation, particular interest is their use in X-ray contrast media.

X-ray contrast media are involved for the visualization of extensive regions of the human body. The contrast reagents are required to have heavy atoms in high concentration to provide the desired opacity in the concerned region. Because of the requirement of high concentrations of these compounds in their use as contrast media, the presence of high proportions of heavier atoms, the desirability of water solubility, and the need for thermal and physiological stability, as well as low toxicity, there are heavy restraints on the type of compounds which may be employed. In addition to the aforementioned restraints, there are concerns with viscosity, osmotic pressure, synthesis, and the like.

Numerous iodinated compounds have been prepared for use as contrast media, but in each case, the compounds demonstrate one or more deficiencies. There has been, therefore, a continuing effort to develop new compounds which provide for better combinations of properties as contrast media.

A significant aspect of the development of a new contrast medium is the development of a process for the preparation of intermediates. The large amount of the compound which is used in an X-ray study makes simple, economic and efficient methods of preparation essential.

2. Description of the Prior Art

U.S. Pat. No. 3,701,771 describes triodobenzoyl sugar amines. Compounds which are presently commercially available include bis-3,5-diacetamido triiodobenzoate (diatrizoate), N,N'-di(1',3'-dihydroxypropyl-2') 5-L-lactoylamido triiodoisophthaldiamide (Iopamidol); and 3-acetamido-5-(N-methyl acetamido) triiodobenzoyl derivative of glucosamine (Metrizamide). Sovak, et al., Radiology 117:717 (1975) describe diiodotriglucosylbenzene. Weitl, et al., J. Med. Chem. 19 353 (1976) describe 2,4,6-triiodo-3-acetamido-5-(N-methyl carboxamido)phenyl β-D-glucopyranoside as a contrast medium. In the Abstracts of the April ACS meeting (1979) is an Abstract by Ranganathan and Sovak, entitled "Synthesis of Carboxamido-triiodophenyl ethers of hexoses from nitroaromatics and their degradation into pentose derivatives." Co-pending U.S. Patent Application Ser. No. 34,099 describes non-glycosidyl carbohydrate ethers of triodo anilines. D-2-amino-2-deoxyerythritol and L-2-amino-2-deoxythreitol are described by Kiss and Sirokman, Helv. Chem. Acta 43, 334 (1960) and A. B. Foster et al, J. Chem. Soc. 1960, 2587, respectively.

SUMMARY OF THE INVENTION

Novel intermediates to small water solubilizing compounds are provided, particularly for novel nonionic X-ray contrast media. The intermediates are dioxepane derivatives having the appropriate amino and hydroxyl functionalities. The dioxepane derivatives provide a useful intermediate for amide formation, with subsequent hydrolysis to the novel contrast media. Products prepared from the subject compound show useful water solubility and low toxicity for contrast media.

The novel nonionic contrast media demonstrate a wide variety of desirable properties for contrast media and are derivatives of symmetrically substituted triiodoisophthaldiamides, with the amide nitrogens trihydroxybutyl substituted and having an acylated amino group at the remaining ring position. The compounds are found to have good water solubility, low toxicity, low protein binding, while meeting many of the other requirements of good contrast media.

The contrast media are readily formulated in a wide variety of conventional formulations for injection as contrast medium for X-ray examination. The compounds also find use as water soluble high density media.

DESCRIPTION OF THE SPECIFIC EMBODIMENTS

The compounds of this invention are 2-substituted-5-aza substituted-6-hydroxy-1,3-dioxepanes, which may be cis, trans, or mixtures thereof. The compounds are prepared from 1,4-dihydroxybutene-2 by preparing the 1,3-dioxepin with an oxo-carbonyl compound, followed by functionalization of the double bond and formation of a vicinal aminoalkanol. Desirably an epoxide is formed followed by ring opening with a nitrogen nucleophile, with the resulting 2-substituted-5-aza substituted-6-hydroxy-1,3-dioxepane trans; the trans compound may be transformed to the cis compound by conventional means. The aza substituted hydroxydioxepane may be used to form the amino group or the amino group formed directly with an amine (includes ammonia) which may then be acylated to provide the desired contrast medium intermediate followed by hydrolysis to provide the N-1,3,4-trihydroxy-butyl-2 group.

The amino substituted compounds of this invention having two hydrogens bonded to nitrogen are used to provide N-substituted triiodobenzenepolycarboxamides, wherein the amide nitrogens are monosubstituted with trihydroxybutyl groups, which serve as contrast media. The contrast media are monomers or dimers, where the dimers are linked through the amino groups substituted at the annular carbon atoms. The monomers will have three iodines, at least 17 carbon atoms, three nitrogen atoms, and at least six hydroxyl groups, generally having from about six to nine oxy groups, of which at least six are hydroxyl. The ratio of carbon to iodine will normally be not greater than seven to one, more usually not greater than about six to one.

The benzene ring will be symmetrically substituted with three iodine atoms, with the remaining annular carbon atoms substituted with from two to three carboxamide groups and from zero to one acylated amino group. Each of the carboxamide nitrogens will be monosubstituted with a trihydroxybutyl group, particularly a 1,3,4-trihydroxybutyl-2 group. The amino group bonded to the annular carbon atom will be acylated with an aliphatic carboxylic acid having at least one carbon atom and not more than about four carbon atoms, usually from two to three carbon atoms, which may have from one to two oxy groups, particularly hydroxy or oxy ether of from one to two, preferably one carbon atom, or with the dimeric compound, the amino group will be substituted with a dibasic acid falling within twice the ranges for the monobasic acid.

For the most part, the contrast media compounds will have the following formula.

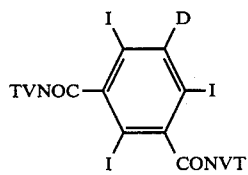

wherein:

D is -CONVT or NVCOE;

T is trihydroxybutyl, particularly 1,3,4-trihydroxybutyl-2;

V is hydrogen or lower alkyl of from 1 to 2 carbon atoms, i.e. methyl or ethyl; and E is hydrogen or an alkyl group of from one to three, usually one to two carbon atoms having from zero to two, usually zero to one oxy groups, which are hydroxyl or ether groups of from one to two carbon atoms, preferably one carbon atom; or, two Es may be taken together to provide a linking group which may be a bond or an alkylene group of from one to four, preferably from one to two carbon atoms and having from zero to four, usually zero to two oxy groups of from zero to two carbon atoms, particularly hydroxy and alkoxy of from one to two carbon atoms.

Illustrative E groups are methyl, ethyl, hydroxymethyl, 1- or 2-hydroxyethyl, 1,2-dihydroxyethyl, or the like. When two Rs are taken together to form a linking group, illustrative linking groups include methylene, ethylene, butylene-1,4, 1,2-dihydroxyethylene, 1,2-dimethoxyethylene, propylene, and 2-oxapropylene.

In preparing the contrast media, various derivatives will be employed where the hydrogens of the hydroxyl groups will be replaced with groups to form ethers or esters. For the most part, these compounds will have the following formula:

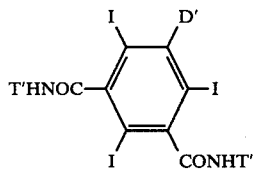

wherein:

D' is —CONHT' or —NHCOE';

T' is a trihydroxybutylene, particularly 1,3,4-trihydroxybutylene or an acetal or ketal thereof, forming a 1,3-dioxepane;

E' is hydrogen or alkyl of from one to three, usually one to two carbon atoms having from zero to two oxy groups which are hydroxy, alkoxy of from one to two carbon atoms, or acyloxy of from one to two, usually one to two carbon atoms, wherein the acyl group is aliphatic carboxy e.g. acetoxy, and wherein two E' groups may be taken together to form a linking group which is a bond or alkylene of from one to four, usually one to three carbon atoms, and from zero to three, usually zero to two oxy groups, having not more than one oxy group per carbon atom, wherein the oxy groups are as defined above for E'.

The compounds of the subject invention are prepared from 1,4-dihydroxybutene-2. The following is a flow diagram of the synthetic procedure:

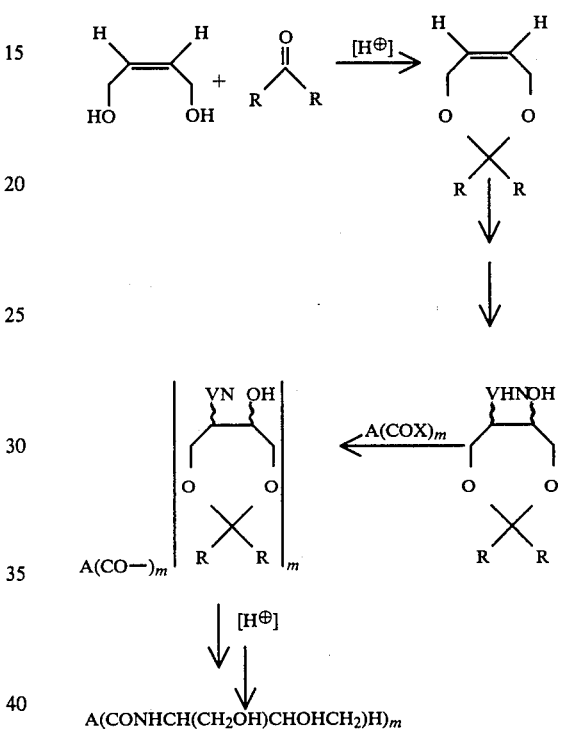

R—hydrogen or an organic radical

V—hydrogn or an organic radical free of interfering groups m—2-3

A—sym-polyiodobenzene having from 0 to 1 annular amino group, normally acylated, and from 2 to 3 carboxyl groups.

The following flow chart describes the process proceeding through an epoxide. [O] can mean any form of oxidation including oxyhalogenation followed by ring closing to an epoxide.

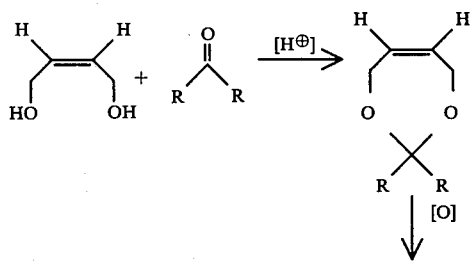

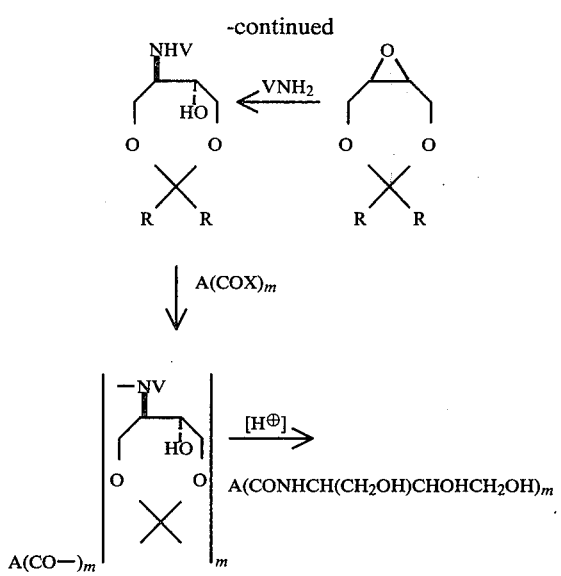

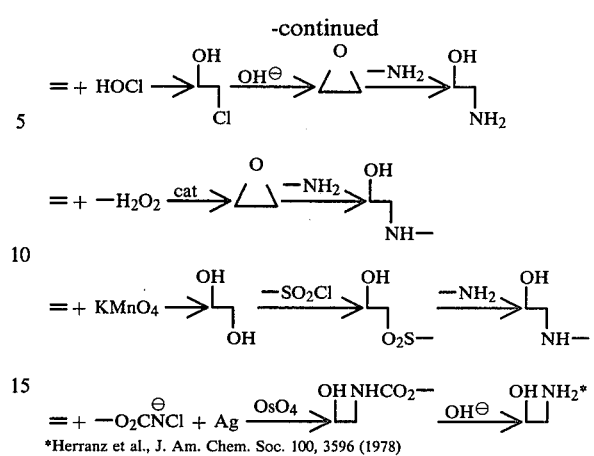

*Herranz et al., J. Am. Chem. Soc. 100, 3596 (1978)

The subject process starts with the readily available 1,4-dihydroxybutene-2. This compound can be reacted with an oxo-carbonyl compound to provide the 1,3-dioxepin. The particular choice of oxo-carbonyl compound is not critical to this invention, since for the subject compound's use in X-ray contrast media, the oxo-carbonyl compound will be removed. Therefore, the oxo-carbonyl compound employed will be one which provides synthetic convenience, economies, absence of interference with the synthetic steps, and ease of removal.

For the most part, the oxo-carbonyl compound will be at least moderately water-soluble, relatively insensitive to the reagents employed in this synthetic procedure, and provide the desired solubility of the reactants during the synthetic procedure. The oxo-carbonyl may be either an aldehyde or ketone, preferably a ketone, and will normally be of from 1 to 12 carbon atoms, more usually of from 2 to 6 carbon atoms, and preferably of from 2 to 4 carbon atoms, more particularly acetone and 2-butanone, and may be aliphatic, alicyclic, aromatic or combinations thereof, and except for the oxo group may be hydrocarbon or substituted hydrocarbon where the substituents will be substantially inert during the synthetic procedure. The 1,3-dioxepin may be prepared by conventional means, particularly combining the oxo-carbonyl and 1,4-dihydroxybutene-2 with the oxo-carbonyl compound or the acetal or ketal thereof, particularly from methanol or ethanol, with a small amount of acid and distilling off either water or alkanol.

The olefin may then be functionalized to a vic-aminoalkanol by a variety of means which may involve epoxidation as a stable intermediate or transiently, direct introduction of the amino an hydroxy functionalities or employing a plurality of steps where the two functionalities are introduced stepwise. The following formulas are illustrative of different reaction schemes to prepare the aminoalkanol:

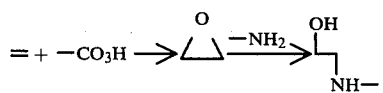

The preferred methods will be epoxidation using hydrogen peroxide or oxyhalogenation, particularly with hypochlorite.

While the above methods describe the use of an amino or substituted amino group as a nucleophile, other nucleophiles could be employed, such as azido.

Epoxidation may be carried out using either organic or inorganic peracids. Particularly, from an economic standpoint, hydrogen peroxide may be employed in a polar solvent under mildly elevated temperature conditions (25°–50° C.), with the peroxide being present in at least stoichiometric amounts, generally at least about two-fold molar excess.

Alternatively, oxyhalogenation may be employed, particularly with chloro, and the halogen displaced, with or without the intermediacy of an epoxide with a nitrogen nucleophile. The oxyhalogenation will normally be carried out in a polar solvent under mildly acidic conditions (−10° to 25° C.). If epoxide formation is desired the alkalinity of the solution is increased and the temperature raised to above ambient, generally in the range of about 50° to 110° C. Usually an excess over stoichiometric of the functionalizing reagent will be employed.

After isolating the epoxide, the amino alcohol may be prepared by aza substitution of the epoxide, using an amine (includes ammonia) under elevated pressures, conveniently autogenous, at temperatures in the range of about 100° to 150° C. Alternatively, azide may be used to form the azido alcohol and the azide reduced to amino by conventional techniques, e.g. catalytic reduction.

The resulting amino alcohol, where the amino group has at least one hydrogen, may now be acylated in accordance with conventional techniques. Conveniently, active acyl groups may be used, such as the halide, mixed anhydride, active ester e.g. N-hydroxy succinimide, or the like. The particular mode of acylation is not critical to this invention.

The protective oxo-carbonyl group may then be removed by any convenient means, conveniently acid hydrolysis.

The 1,2-dihydroxybutene-2 employed will be the cis compound, since the trans does not form the 1,3-dioxepin. The synthetic procedure described above, therefore, provides the trans-amino alcohol, which upon hydrolysis of the 1,3-dioxepane provides the threityl derivative. If the erythrityl derivative is desired, the 5-amino-6-hydroxy-1,3-dioxepane may be employed for inversion of either the amino group or the hydroxyl group to provide the cis-compound, which upon hydrolysis of the 1,3-dioxepane will directly provide the erythritylamine. Techniques for inverting either amino groups or hydroxyl groups are well known in the prior art. For example, oxazolines or oxazolones may be prepared by acylation of the amino group and by activation of the hydroxyl, for example, by preparing sulfonate esters e.g. tosylate, mesylate or brosylate. Alternatively, techniques exist for direct formation of the cis compound, Herranz, supra. Thus, the subject process allows for the formation of either the erythrityl or threityl amides.

For the most part, the compounds of this invention will have the following formula:

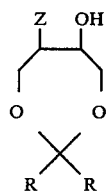

wherein:

Z is azido or HNW, wherein W is hydrogen or a substituted or unsubstituted organic radical of from 1 to 12, usually 1 to 8 carbon atoms, which may be hydrocarbon, either aliphatically saturated or unsaturated having from 0 to 2 sites of aliphatic unsaturation, particularly ethylenic, being aliphatic, alicyclic, aromatic or combinations thereof, usually having not more than one ring; or may have from 1 to 3, usually 1 to 2 substituents, which may be non-oxo-carbonyl, unreactive halo e.g. fluoro or bonded to an aromatic annular carbon atom, oxy e.g. hydroxy, amino, or oxo carbonyl; usually there will be up to 6, more usually up to 4 heteroatoms, which are oxygen, nitrogen and halogen;

the Rs may be the same or different and are hydrogen or an organic radical, which may be hydrocarbon or substituted hydrocarbon, where any substituents are inert and will not interfere with the steps of the process in preparing the contrast media, including preparing the precursors of the subject compounds;

R may be aliphatic, alicyclic, aromatic, heterocyclic or combinations thereof or the two Rs may be taken together to form a ring, but preferably R will be aliphatically saturated, more preferably alkyl of from 2 to 4, more usually of from 2 to 3 carbon atoms. It should be appreciated that the portion of the molecule defined by R and the carbon to which the two Rs are attached is not a critical aspect of the subject invention, primarily providing a protective group for the terminal hydroxyls of the tetritol amine, which group is removed in the preparation of the contrast media. Therefore, the particular choice of oxo-carbonyl for preparation of the 1,3-dioxepane is primarily one of convenience. Nevertheless, in view of the nature of the reactions, the solvents employed, ease of isolation and the like, lower alkyl groups will be the most desirable.

It should be noted that the particular stereochemistry is not indicated in the formula.

Illustrative compounds include:
2,2-dimethyl-5-amino-6-hydroxy-1,3-dioxepane;
2-ethyl-2-methyl-5-amino-6-hydroxy-1,3-dioxepane;
2-phenyl-5-amino-6-hydroxy-1,3-dioxepane;
2-benzyl-5-amino-6-hydroxy-1,3-dioxepane;
spiro[cyclohexyl-1,2'-5'-amino-6'-hydroxy-1',3'-dioxepane];
2-methyl-2-methoxymethyl-5-amino-6-hydroxy-1,3-dioxepane; and
2,2-dipropyl-5-amino-6-hydroxy-1,3-dioxepane. (either cis- or trans-)

When R is other than hydrogen, the total number of carbon atoms of the two Rs will generally not exceed 12, more usually not exceed 10, generally ranging from about 2 to 8, more usually ranging from about 2 to 6.

By employing the compounds of the subject invention for the preparation of contrast media, a number of advantages ensue. First, an efficient and economical process is provided for preparing a critical intermediate. Secondly, the problem of acylation of the amine with the plurality of other active functional groups is avoided since the vicinal aminoalcohol will provide the amide, regardless of whether the hydroxyl or the amino groups are acylated first. By virtue of employing the 1,3-dioxepane aminoalcohol, rather than the trihydroxybutylamine, a cleaner, economic and more efficient acylation reaction is obtained. Thus, the high molecular weight polyiodo-substituted aromatic acids are utilized efficiently and in high yield.

Turning now to a consideration of the contrast media, it is understood that many of the contrast media may employ stereoisomers. Either the racemic or active forms, D, L, or meso may be employed as to each of the substituents on the ring.

Illustrative acyl groups bonded to the annular amine of the contrast media, either as precursors or in the final product include acetyl, glycolyl, methoxyacetyl, lactoyl, propionyl, acetoxyglycoyl, 2-acetoxypropionyl, malondioyl, succindioyl, tartardioyl, and the like.

Illustrative contrast media products employing the precursors of the subject invention include:

TABLE I

N,N'-bis(1',3',4'-trihydroxybutyl-2')-2,4,6-triiodo-5-acetamidoisophthaldiamide
N,N'-bis(1',3',4'-trihydroxybutyl-2')-2,4,6-triiodo-5-glycolamidoisophthaldiamide
N,N'-bis(1',3',4'-trihydroxybutyl-2')-2,4,6-triiodo-5-lactamidoisophthaldiamide
N,N'-bis(1',3',4'-trihydroxybutyl-2')-2,4,6-triiodo-5-methoxyacetamidoisophthaldiamide
bis-N,N'-(N'',N'''-bis(1',3',4'-trihydroxybutyl-2')-2,4,6-triodoisophthaldiamide-5-yl) tartardiamide
bis-N,N'-(N'',N'''-bis(1',3',4'-trihydroxybutyl-2')-2,4,6-triiodoisophthaldiamide-5-yl) glutardiamide
(1',3',4'-Trihydroxybutyl-2' may be D, L or DL erythrityl or threityl.)

As a result of employing the precursors of the subject invention, the resulting contrast media compounds have one or more of the following desirable properties. The compounds have lower toxicity and higher stability as compared to polyiodo non-ionic contrast media conventionally used, particularly in the United States, acceptable viscosity and water solubility, high iodine concentration possible, low osmotic pressure, and low degree of interference with the microcirculation.

When employed as X-ray contrast media, they will normally be employed in combination with a pharmaceutically acceptable carrier, wherein the contrast media compound will be present in concentrations of about 20–500 mg I/ml, more usually 100–400 mg I/ml. The type and quantity of contrast agent to be administered is preferably such as to stay in the system only for about 2 to 3 hrs., although both shorter and longer residence times are normally acceptable.

Besides use as contrast media, the subject contrast media because of their high molecular weight and density, may find uses for a variety of other purposes. The subject compounds can be used in biological techniques, where cells are handled in solutions of high specific gravity, for example, in centrifugation or differential flotation, since their low osmolality reduces the osmotic lysis of the cells as compared to ionic compounds. In addition, the subject compounds can be used to provide density gradients for molecular weight separation by centrifugation or the like; can be prepared with radioactive iodine to be used as radioactive markers, or may be used to label compounds with iodine as radioactive labels, fluorescent quenchers, or the like.

The subject compounds provide a useful route to tetritol amines, where the amino group may be substituted or unsubstituted allowing for variation in its hydrophilicity-hydrophobicity. Thus, the tetritol amines may be modified by polymerization with alkylene oxides to form non-ionic detergents, may be used directly as buffers, or the like. Furthermore, modification of the nitrogen can be employed to vary the physical, chemical and physiological properties of the parent compound and derivatives thereof.

The following examples are offered by way of illustration and not by way of limitation.

EXPERIMENTAL (All temperatures not otherwise indicated are in centigrade. All parts not otherwise indicated are by weight, except for mixtures of liquids which are by volume. The following abbreviation is used: DMA=N,N-dimethylacetamide.)

1. 4,4-Dimethyl-3,5,8-trioxabicyclo-[5.1.0]-octane (III)

The subject compound was synthesized following a published procedure. [Ref. Fried and Elliot, J. Org. Chem., 41, 2469 (1976)].

A. To a suspension of m-chloroperbenzoic acid (74% pure; 78.15 g; 0.33 mole) in methylene chloride (600 ml), was added a solution of 2,2-dimethyl-4,7-dihydro-1,3-dioxepin (II) (41.0 g, 0.32 mole) in methylene chloride (200 ml) during 30 min at room temperature. The mixture was refluxed for 8 hrs and then cooled in ice for 1 hr. The precipitated solid was filtered off and the organic filtrate was washed with 10% aqueous sodium sulfite ($2 \times 100$ ml), saturated aqueous sodium bicarbonate ($3 \times 500$ ml), 5% aqueous sodium hydroxide ($2 \times 250$ ml) and brine ($2 \times 200$ ml) and dried (MgSO$_4$). Removal of the solvent followed by vacuum distillation of the residual oil gave the epoxide product (III) as a colorless liquid. 36.94 g (80% yield). b.p. 90°–92°/11 mm.

The following is an improved method employing the more economical hydrogen peroxide as the epoxidizing agent.

B. To a stirred solution of 2,2-dimethyl-4,7-dihydro-1,3-dioxepin (151.4 g, 1.18 mole) in methanol (500 ml) was added anhydrous sodium carbonate (85 g), followed by acetonitrile (150 ml). This suspension was treated with aqueous hydrogen peroxide (30%; 315 ml, 2.78 mole) dropwise at such a rate that the temperature was maintained at 40°. After 5 hr. at 40°, the reaction mixture was poured into brine (1.5 l) and the solution was extracted with n-butanol. The organic layer was washed with brine, dried, and, then, freed of the solvent in vacuo. Vacuum distillation of the residue yielded the product (III) as a colorless liquid (114 g) (67% yield).

C. To a suspension of sodium carbonate (37 g, 0.35 mole) in a mixture of the dioxepin (II) (158.7 g, 1.26 mole), benzonitrile (127.9 g, 1.26 mole) and methanol (150 ml), was added 30% aqueous hydrogen peroxide (42.2 g, 1.24 mole) during 30 min at such a rate that the temperature stayed below 80°. The mixture was kept at 80° with an oil bath for 2 hr, by which time 99% of the hydrogen peroxide added had reacted. The mixture was decanted and, then, subjected to fractional distillation first at 60 mm, then at 20 mm and finally at 6 mm. The fraction boiling at 75°–85° at 6 mm was refractionated at 6 mm to obtain the product (III) as a colorless liquid. (125.5 g) (70% yield). b.p. 82°–87°/6 mm.

D. To an ice-cold (5°), stirred solution of the dioxepin (II) (12.81 g, 0.1 mole) in aqueous t-butanol (50%; 50 ml) adjusted to pH 6.0 with dilute sulfuric acid, was added t-butyl hypochlorite (11.3 g, 0.105 mole), while the pH was maintained at 6.0. The reaction mixture was allowed to rise to room temperature and stirred for 4 hrs with protection from light. Sodium bisulfite (200 mg) was added to the reaction mixture, followed by 50% aqueous sodium hydroxide to bring the pH to 12. The reaction mixture was heated at 100° for 1 hr and then cooled. The upper t-butanol layer was separated and the aqueous layer was extracted with t-butanol ($3 \times 20$ ml). The combined organic layers were dried (Na$_2$CO$_3$). Solvent removal, followed by fractional distillation, gave the epoxide product (III) as a colorless oil in $\simeq$80% yield.

E. To an ice-cold (0°–5° C.), stirred solution of the dioxepin (150.0 g, 1.18 mole) in a mixture of t-butanol (250 ml) and water (150 ml) was added, during 1 hr, powdered calcium hypochlorite (59%; 150 g, 0.62 mole), portionwise, with continuous bubbling of carbon dioxide through the solution. After 30 min, aqueous 50% sodium hydroxide (160 g, 2 moles) was added and the suspension was refluxed, with stirring, using an oil bath (100°) for 1.5 hr. The mixture was filtered and the organic layer of the filtrate was separated. The aqueous layer was extracted once with t-butanol (50 ml) and the combined organic layers were washed with brine ($3 \times 20$ ml). The combined washings were re-extracted once with t-butanol (50 ml). The solvent was removed from the organic layer in a Rotovapor at 70° and 100 mm. The residue was subject to fractional distillation and the product (III) was isolated as a colorless oil. (116.1 g, 68% yield) b.p. 65°–67°/5 mm.

2. trans-2,2-Dimethyl-6-hydroxy-5-amino-1,3-dioxepane (IV)

A. A steel bomb was charged with liquid ammonia (60 ml) with cooling in an isopropanol-dry ice bath maintained at $-70°$ C. The epoxide (III) (21.46 g, 0.15 mole) was added to it, followed by water (2.70 ml, 0.15 mole). The bomb was sealed and, then, heated in an oil bath at 120° for 4 hr. The bomb was cooled, opened and the ammonia was allowed to evaporate. The crude residue was triturated with ether, chilled, and the crystalline product was isolated by filtration. The amine (IV) was obtained as white prisms. (18.78 g, yield 87%). m.p. 81.5°–82.5°.

B. 2,2-Dimethyl-4, 7-dihydro-1, 3-dioxepin (8.63 g, 59.8 mmols) was placed in a 500 ml Parr high pressure reaction vessel. To this, conc. ammonium hydroxide (45 ml) is added. The bomb is closed and heated in an oil bath (vent open) to 70° C. At this point the vent is closed. Heating is continued as quickly as possible to 145° C. The pressure reads 65 psi, when the system equilibrates. After 45 min, the vessel is cooled to room temperature and opened. The reaction mixture is transferred to a 250 ml round bottom flask and the ammonia removed under vacuum (H₂O aspirator). The H₂O is evaporated off, leaving a yellow viscous oil, which is further dried by co-distillation with absolute ethanol. The residual oil is triturated at −20° C. with anhydrous ethyl ether (15–20 ml). The ether is removed by filtration and the crude product (IV) (7.92 g) is recrystallized from ethyl acetate/hexane. Yield: 82%.

3. Synthesis of 2,4,6-triiodo-5-amino-isophthalic acid bis-chloride (V)

Compound (V) was prepared from 5-amino isophthalic acid by iodination, followed by chlorination, according to methods similar to published procedures. (Wallingford, et al, J. Am. Chem. Soc., 74, 4365 (1952). The bis-chloride (V) was purified by crystallization from benzene under mild conditions.

4. Acylation of the bis-chloride (V)

A solution of the bis-chloride (V) in DMA was treated with 5 equivalents of acetyl chloride at room temperature overnight. After pouring the reaction mixture into ice water the product (Va) was filtered and dried. This product (98% pure) was used without further purification.

Use of O-acetyl glycolyl chloride or O-acetyl-DL- or L-lactoyl chloride in an analogous manner gave (VIb) and (VIc).

5. Amination of the acylated bis-chlorides (VI)

(i) 2,4,6-triiodo-5-acetylamino-isophthalic acid bis-N,N' (trans-2,2-dimethyl-6-hydroxy-1,3-dioxepane-5-yl)diamide (VIIa)

The N-acetyl-bis-chloride (VIIa) (0.6 g, 1.0 mMol) was stirred with 2.5 equivalents of trans-5-amino-2,2-dimethyl-6-hydroxy-1,3-dioxepane IV in DMA (5 ml) at 50° for 5 hr. The DMA was evaporated and the residue was purified by column chromatography over silica gel using chloroform-methanol mixture to obtain the product VIIa (0.93 g, quantitative yield) as a colorless foam.

The 5-acetoxyacetylamino- and 5-(2-acetoxy-DL-or L-propionylamino)-analogs (VIIb) and (VIIc) respectively, were synthesized similarly in 87% and 95% yields.

Alternatively, after removal of the DMA, the residue is dissolved in aq. ethanol and the pH adjusted to 6.0 with dil HCl. After solvent evaporation, ethyl acetate is added to the residue, when most of the hydrochloride of the excess amine crystallizes out and is filtered off. The ethyl acetate layer is then washed with brine, dried and the solvent removed to yield VIIc.

6. Deprotection of the bis-amides (VII)

(a) 2,4,6-triiodo-5-acetylamino-isophthalic acid bis-N,N' (1,3,4-trihydroxy-threo-but-2-yl)-amide (VIIIa)

The protected bis-amide (VIIa) mg, 0.71 mMol) was stirred with 90% aqueous trifluoroacetic acid (4 ml) for 1 hr. The solvent was removed and the residue purified by column chromatography over Diaion HP-20 resin using aqueous ethanol mixture. The product (313 mg, 55% yield) was obtained as white prisms by crystallization from water. m.p. 246°–47°.

(b) 2,4,6-triiodo-5-hydroxyacetylaminoisophthalic acid-bis-N,N'-(1,3,4-trihydroxy-threo-but-2-yl)-amide (VIIIb).

The protected bis-amide (VIIb) (1.21 g, 1.28 mMol) was deacetylated with sodium hydroxide at pH 11 and then treated with 90% trifluoroacetic acid as above. After purification through chromatography over Diaion HP-20 column the product (0.86 g, 82% yield) was crystallized from aqueous methanol.

(c) 2,4,6-triiodo-5-(2-DL or L-hydroxypropionylamino)-isophthalic acid-bis-N,N'-(1,3,4-trihydroxy-threo-but-2-yl)-amide (VIIIc)

This compound was synthesized as described for the hydroxyacetyl analog (VIIIb). The product was obtained in 69% yield as a colorless glassy solid. The product had a solubility in water at 20° C. of >400 mgI/ml and at 37° C. a viscosity of 6.6 cps at 300 mgI/ml.

7. N,N'-bis-(2,4,6-triiodo-3,5-bis-chlorocarbonylphenyl)-malondiamide (IX)

The bis-chloride (V) (2.45 g, 4.1 mmol) was stirred with malonoyl dichloride (330 ml, 3.2 mmol) in dioxane (10 ml) at 95° for 1 hr. On cooling the product crystallized out and was collected by filtration and dried. 1.71 g, yield 66%.

8. N,N'-bis-[2,4,6-triiodo-3,5-bis-{N,N'-(trans-2,2-dimethyl-6-hydroxy-1,3-dioxepan-5-yl)}-carbamoylphenyl]-malondiamide (X)

The tetra-kis-chloride (IX) was treated as above with trans-2,2-dimethyl-6-amino-5-hydroxy-1,3-dioxepane IV to obtain the product after chromatography over Silica gel. 8.53 g, 89% yield.

9. N,N'-bis-[2,4,6-triiodo-3,5-bis-{N,N'-(1,3,4-trihydroxy-threo-but-2-yl)}-carbamoyl-phenyl]-malondiamide (XI)

The protected tetra-kis-amide (X) was treated with 90% aqueous trifluoroacetic acid at room temperature for 1 hr. The solvents were removed and the residue in water after neutralization to pH 5.0 with Dowex-1-OH⊖ resin, was purified over Diaion-HP 20 resin using aqueous ethanol mixture to obtain the product as a colorless solid. 72% yield. This was crystallized from water.

10. Synthesis of 2,4,6-triiodo-5-N-methylaminoisophthalic acid-bis-chloride (XII)

Compound (XII) was prepared from 5-N-methylaminoisophthalic acid (20.05 g, 35 mmole) by treatment with thionyl chloride by conventional procedures. The product (XII) was obtained as a tan colored solid in 54% yield.

11. Acetylation of the bis-chloride (XII)

A solution of the bis-chloride (XII) (11.5 g, 15.7 mmole) in DMA (40 ml) was treated with 5 equivalents of acetyl chloride at room temperature overnight. The precipitated solid was filtered and washed successively with water, aqueous sodium bicarbonate and water. The product (XIII) was dried. Yield 82%.

12. 2,4,6-Triiodo-5-N-methylacetylamino-isophthalic acid-bis-N,N'-(trans-2,2-dimethyl-6-hydroxy-1,3-dioxepan-5-yl)-amide (XIV)

The N-methylacetyl-bis-chloride (XIII) (4.20 g, 6.4 mmole) was stirred with 4 equivalents of trans-5-amino-2,2-dimethyl-6-hydroxyl-1,3-dioxepane (IV) in DMA (30 ml) at 50° for 8 hr. The DMA was evaporated off in vacuo and the residue was purified by column chromatography over silica gel using chloroform-methanol mixture. The product (XIV) was obtained as a colorless foam in 89% yield.

13. 2,4,6-Triiodo-5-N-methylacetylamino-isophthalic acid-bis-N,N'-(1,3,4-trihydroxy-threo-but-2-yl)-amide (XV)

The protected bis-amide (XIV) (9.46 g, 10.5 mmole) was dissolved in ice cold 90% aqueous trifluoroacetic acid (60 ml) and the solution was stirred at room temperature for 1 hr. The solvents were removed in vacuo and the residue was coevaporated with ethanol four times. An aqueous solution of the residue was neutralized with Dowex-1-OH$^{\ominus}$ resin and then purified by column chromatography over diaion-HP-20 resin using water-ethanol mixture. The product (XV) was obtained as a colorless glassy solid. (4.79 g) (yield 56%).

14. N,N'-bis-Methyl-N,N'-bis-[2,4,6-triiodo-3,5-bis-{N,N'-(2,2-dimethyl-6-hydroxy-1,3-dioxepan-5-yl)}-carbamoyl phenyl]malondiamide (XVII)

A solution of the N,N'-bis-methyl-tetra-kis-chloride (XVI) (7.0 g, 5.44 mmole) in DMA (30 ml) was treated with tributylamine (5.2 ml, 21.7 mmole), followed by trans-2,2-dimethyl-5-amino-6-hydroxyl-1, 3-dioxepane (IV) (5.25 g, 32.6 mmole) at 50° for 6 hr. The solvent was removed in vacuo and the residue was chromatographed over silica gel using chloroform-methanol mixture. One of the expected geometric isomers of the product (XVII) was obtained in the pure form (5.20 g) (53% yield) from the initial fractions. The later fractions yielded more of the product (XVII) (2.25 g) (23% yield) as a mixture of isomers. The total yield of the isolated product was 76%.

15. N,N'-bis-Methyl-N,N'-bis [2,4,5-triiodo-3,5-bis-{N,N'-(1,3,4-trihydroxy-threo-but-2-yl)}-carbamoylphenyl]malondiamide (XVIII)

Deprotection of the tetra-kis-amide (XVII) (4.56 g, 2.5 mmole) was achieved by treatment with 90% aqueous trifluoroacetic acid as described above in experiment XII. The product was obtained as a colorless solid. (2.93 g) (yield 72%).

16. 2,4,6-Triiodo-trimesic acid tris-N,N',N''-trans-(2,2-dimethyl-6-hydroxy-1,3-dioxepan-5-yl)amide (XX)

2,4,6-Triiodotrimesic acid tris-chloride (XIX) (15.0 g, 23.3 mmole) was stirred with 7.5 equivalents of trans-5-amino-2,2-dimethyl-6-hydroxy-1,3-dioxepane (IV) in DMA (70 ml) at 50° for 17 hr. The DMA was evaporated off in vacuo. The residual syrup was dissolved in aqueous ethanol and then neutralized with 2 N HCl. The solvents were removed and a solution of the residue in chloroform was washed with brine. Removal of the solvent from the organic layer gave the product as a pale yellow syrup.

17. 2,4,6-Triiodotrimesic acid tris-N,N',N''-(1,3,4-trihydroxy-threo-but-2-yl)amide (XXI)

Deprotection of the crude tris-amide (XX) obtained in experiment 16 was achieved by treatment with 90% aqueous trifluoroacetic acid as described in experiment 13. The product was obtained as an off-white solid (16.48 g) (yield 79%).

In order to demonstrate the low toxicity of the subject compounds, the dimer compound XI was employed as illustrative. Employing conventional procedures, the following tests were carried out and compared with known commercially available contrast media. The following tables indicate the results.

| Pharmacological Properties of Novel Contrast Media | | | |
|---|---|---|---|
| Systemic Toxicity: | $LD_{50}$ (gI/kg bw) of compound injected intravenously in groups of 10 mice. | | |
| | Iopamidol ® | Metrizamide ® | VIIIc |
| gI/kg bw | 18.7 | 12.1 | 21.3 |
| Neurotoxicity: | Neural deficits after intracisternal injections in rats with chronically implanted cannulas into the right ventricle. | | |
| Dose | Metrizamide | Iopamidol | VIIIc |
| 40 mg I | Disturbed alertness, locomotion, occasional convulsions | Disturbed alertness & locomotion, irritability | Normal |
| Deficit Scores: | 25.3 ± 10.1 | 1.75 ± 0.96 | 0 |
| 60 mg I | Convulsions, severe neurological deficits, death | Deficits, convulsions | Irritability |
| Deficit Scores: | 84.2 ± 12.3 | 22.0 | 3.0 ± 1.73 |
| 100 mg I | Death | Death | Some Deficits |
| Deficit Scores: | —n/a | —n/a | 26 ± 3.2 |
| Dose: | | XV | XVIII |
| 40 mg I | | Normal | Normal |
| Deficit Scores: | | 0 | 0 |
| 60 mg I | | Some Deficits | Normal |
| Deficit Scores: | | 23 | 0 |
| 100 mg I | | Some Deficits Death | Normal |
| Deficit Scores: | | — | 0 |

0 = normal
Deficit scores were calculated on the basis of a preset rating (average of 10 rats).
Concl: These results indicate that VIIIc and XVIII are the least toxic of all contrast media currently known.

| Toxicity: | Aversive conditioning in rats: (Testing for preference/avoidance after an injection into the lateral ventricle via a chronically implanted cannula) (Average from a group of 10 rats) | | |
|---|---|---|---|
| | Metrizamide | Iopamidol | VIIIc |
| % Aversion: | 29.8 | 24.6 | 9.4 |
| Aversion expressed in relation to Metrizamide | 1 | 1.2 times less aversive | 3.4 times less aversive |

In this behavioral study, the rats have shown more aversion

-continued towards Iopamidol and Metrizamide than towards VIIIc.
Cell Toxicity: (LD₅₀ at 4' of a standardized culture of a
protozoan *Blepharisma americ.*)

| | Metrizamide | Iopamidol | VIIIc |
|---|---|---|---|
| LD₅₀ in mg I/ml: | 133 | 136 | 148 |

Concl: VIIIc has lower toxicity than Iopamidol and Metrizamide.

In accordance with the subject invention, a novel efficient and economic process is provided for producing tetritol amines in a form which they may be conveniently acylated to provide contrast media. The cyclic 1,3-dioxepane derivative greatly enhances the ease of preparation of the various intermediates, as well as their isolation and purification. In the final step, the protective group is readily removed to provide the desired contrast medium.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

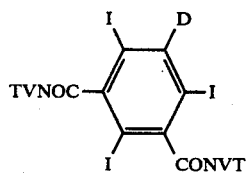

wherein:
D is —CONVT or NVCOE;
T is trihydroxybutyl;
V is hydrogen or lower alkyl of from 1 to 2 carbon atoms;
E is hydrogen, an alkyl group of from one to three carbon atoms having from zero to two oxy groups, which oxy groups are hydroxyl or ether groups of from one to two carbon atoms or two Es may be taken together to provide a linking group which may be a bond or an alkylene group of from one to four carbon atoms having from zero to four oxy groups, which oxy groups are hydroxy or alkoxy of from one to two carbon atoms.

2. A compound according to claim 1, wherein D is NVCOE V is hydrogen and the two Es are taken together to define an alkylene group of from one to four carbon atoms and zero to four oxy groups, and wherein T is 1,3,4-trihydroxybutyl-2.

3. A compound according to claim 2, wherein the two Es are taken together to define methylene.

4. A compound according to claims 1, 2 or 3, wherein T is threityl.

5. A compound according to claim 1, wherein E is an alkyl group of from 1 to 3 carbon atoms and 0 to 2 oxy groups.

6. A compound according to claim 5, wherein E is 1-hydroxyethyl.

7. A compound of the formula:

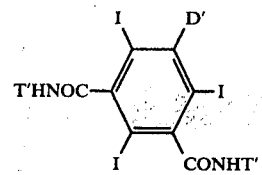

wherein:
D' is -CONHT' or -NHCOE';
T' is 1,3,4-trihydroxybutyl-2 or an acetal or ketal thereof, wherein said acetal or ketal is formed from an aldehyde or ketone respectively of from 1 to 12 carbon atoms; and
E is hydrogen, or alkyl or from one to three carbon atoms having from zero to two oxy groups, wherein said oxy groups are of from zero to three carbon atoms, and wherein two E' groups may be taken together to form a bond or alkylene group of from one to four carbon atoms having from zero to three oxy groups of from zero to two carbon atoms, wherein oxy is hydroxy or alkoxy.

8. A compound according to claim 7, wherein D' is NHCOE and the two E's are taken together.

9. A compound according to claim 8, wherein the two E's taken together define methylene.

10. A compound according to any of claims 7 to 9, wherein T' is 1,3,4-trihydroxybutyl-2.

11. A compound according to claim 7, wherein E' is alkyl of from one to two carbon atoms having from 0 to 1 hydroxy group.

12. A compound according to claim 11, wherein T' is 1,3,4-trihydroxybutyl-2.

13. A compound according to claim 12, wherein T' is the threityl stereoisomer.

14. A compound according to claim 7 of the formula:

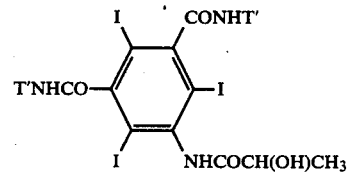

wherein T' is 1,3,4-trihydroxybutyl-2.

15. A compound according to claim 14, wherein T' is the threityl stereoisomer.

16. A compound according to claim 7, wherein D' is —CONHT' and T' is 1,3,4-trihydroxybutyl-2.

17. A compound according to claim 16, wherein T' is the threityl stereoisomer.

18. A compound according to claim 7 of the formula:

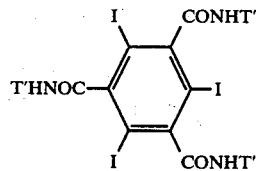

wherein T' is 1,3,4-trihydroxybutyl-2.

19. A compound according to claim 18, wherein T' is the threityl isomer.

20. A compound according to claim 1, wherein D is —NVCOE, V is methyl, the two Es are taken together to define an alkylene group of from 1 to 4 carbon atoms and zero to 4 oxy groups, and T is 1,3,4-trihydroxybutyl-2.

21. A compound according to claim 20, wherein the 2 Es are taken together to define methylene.

22. A compound according to claim 1, wherein D is —NVCOE, V is methyl and E is alkyl of from 1 to 3 carbon atoms.

23. A compound according to claim 22, wherein E is methyl.

24. An X-ray contrast medium formulation having a compound according to any of claims 11 to 17 or 18 in a pharmaceutically acceptable carrier in a concentration of about 20–500 mg I/ml.

25. An X-ray contrast medium according to claim 24, wherein said compound is according to claim 14.

26. An X-ray contrast medium formulation according to claim 24, wherein said compound is according to claim 16.

27. An X-ray contrast medium formulation according to claim 24, wherein said compound is according to claim 18.

28. An X-ray contrast medium formulation having a compound according to claim 1, wherein T is 1,3,4-trihydroxybutyl-2, in a pharmaceutically acceptable carrier in a concentration of about 20–500 mg I/ml.

29. A formulation according to claim 28, wherein D is —NVOE and the two E's are taken together.

30. A compound according to claim 10, wherein T' is the erythrityl stereoisomer.

31. A compound according to claim 1, wherein T is the erythrityl stereoisomer.

* * * * *